(12) United States Patent
Berdahl et al.

(10) Patent No.: US 10,154,926 B1
(45) Date of Patent: Dec. 18, 2018

(54) METHODS OF USING EYE MONITORING AND PRESSURIZATION SYSTEMS

(71) Applicant: John Berdahl, Sioux Falls, SD (US)

(72) Inventors: John Berdahl, Sioux Falls, SD (US); Richard Cornelius, Wayzata, MN (US); Vance Michael Thompson, Sioux Falls, SD (US)

(73) Assignee: John Berdahl, Sioux Falls, SD (US)

( * ) Notice: Subject to any disclaimer, the term of this patent is extended or adjusted under 35 U.S.C. 154(b) by 0 days.

(21) Appl. No.: 15/688,043

(22) Filed: Aug. 28, 2017

Related U.S. Application Data

(63) Continuation of application No. 15/345,053, filed on Nov. 7, 2016, which is a continuation of application
(Continued)

(51) Int. Cl.
*A61F 5/00* (2006.01)
*A61F 9/007* (2006.01)
(Continued)

(52) U.S. Cl.
CPC ............ *A61F 9/00781* (2013.01); *A61B 3/16* (2013.01); *A61B 5/032* (2013.01); *A61B 5/4836* (2013.01); *A61B 5/6803* (2013.01); *A61F 9/029* (2013.01)

(58) Field of Classification Search
CPC ........ A61F 9/00781; A61F 9/029; A61F 9/04; A61F 9/028; A61F 9/068; A61F 2009/021; A61B 3/16; A61B 5/6803; A61B 5/032
See application file for complete search history.

(56) References Cited

U.S. PATENT DOCUMENTS

| 2,555,636 A | 6/1951 | Felts et al. |
| 4,305,399 A | 12/1981 | Beale |

(Continued)

FOREIGN PATENT DOCUMENTS

| CN | 203989163 U | 12/2014 |
| WO | WO-2007012008 A2 | 1/2007 |

(Continued)

OTHER PUBLICATIONS

"U.S. Appl. No. 13/790,048, Final Office Action dated Feb. 5, 2015", 13 pgs.

(Continued)

*Primary Examiner* — Eric Rosen
*Assistant Examiner* — Mikail Mannan
(74) *Attorney, Agent, or Firm* — Schwegman, Lundberg & Woessner, P.A.

(57) ABSTRACT

Assemblies and methods for modifying an intraocular pressure of a patient's one or both eyes are disclosed. The assemblies and methods can be used to treat, inhibit, or prevent ocular conditions such as glaucoma, high intraocular pressure, optic disc edema, idiopathic intracranial hypertension, zero-gravity induced papilledema, and other optic pressure related conditions. An assembly can include a goggle including at least one cavity, a pump in fluid communication with the at least one cavity, and a control mechanism. The control mechanism can be operatively coupled to the pump and can maintain a target pressure or target pressure range in the at least one cavity, which, when the assembly is worn by a patient, is the area between a patient's eye(s) and wall surfaces of the goggle. Controlling the pressure over the outer surfaces of the patient's eye(s) can drive a desired change in the intraocular pressure of the eye(s).

20 Claims, 4 Drawing Sheets

Related U.S. Application Data

No. 14/800,018, filed on Jul. 15, 2015, now Pat. No. 9,498,380, which is a continuation of application No. 13/790,048, filed on Mar. 8, 2013, now Pat. No. 9,125,724.

(60) Provisional application No. 61/609,078, filed on Mar. 9, 2012.

(51) Int. Cl.
*A61B 5/00* (2006.01)
*A61F 9/02* (2006.01)
*A61B 3/16* (2006.01)
*A61B 5/03* (2006.01)

(56) References Cited

U.S. PATENT DOCUMENTS

| | | | |
|---|---|---|---|
| 4,387,707 A | 6/1983 | Polikoff | |
| 4,724,843 A | 2/1988 | Fisher | |
| 4,907,595 A | 3/1990 | Strauss | |
| 5,523,808 A | 6/1996 | Kohayakawa | |
| 5,601,548 A | 2/1997 | Smith et al. | |
| 5,625,426 A | 4/1997 | Liu | |
| 5,927,281 A | 7/1999 | Monteleone et al. | |
| 5,951,477 A | 9/1999 | Ragaluskals et al. | |
| 6,129,682 A | 10/2000 | Borchert et al. | |
| 6,673,014 B2 | 1/2004 | Badchi et al. | |
| 6,814,966 B1 | 11/2004 | Wax et al. | |
| 7,122,007 B2 | 10/2006 | Querfurth | |
| 8,408,204 B2 | 4/2013 | Lurie | |
| 9,125,724 B2 | 9/2015 | Berdahl et al. | |
| 9,498,380 B2 | 11/2016 | Berdahl et al. | |
| 2003/0088260 A1* | 5/2003 | Smedley | A61F 9/0017 606/169 |
| 2004/0111050 A1 | 6/2004 | Smedley et al. | |
| 2004/0237969 A1 | 12/2004 | Fuller | |
| 2007/0123796 A1* | 5/2007 | Lenhardt | A61B 5/031 600/561 |
| 2007/0282405 A1 | 12/2007 | Wong, Jr. et al. | |
| 2008/0086048 A1* | 4/2008 | Dupps, Jr. | A61B 3/10 600/405 |
| 2008/0171953 A1 | 7/2008 | Mische | |
| 2009/0043365 A1 | 2/2009 | Friedland et al. | |
| 2010/0056935 A1 | 3/2010 | McKinley et al. | |
| 2011/0022010 A1 | 1/2011 | Grenon et al. | |
| 2011/0137182 A1 | 6/2011 | Bellezza et al. | |
| 2012/0222201 A1 | 9/2012 | Dondero | |
| 2013/0041245 A1* | 2/2013 | Cerboni | A61B 5/6821 600/398 |
| 2013/0072828 A1 | 3/2013 | Sweis et al. | |
| 2013/0144185 A1* | 6/2013 | Fuller | A61B 3/16 600/561 |
| 2013/0144195 A1 | 6/2013 | Fuller et al. | |
| 2013/0211285 A1 | 8/2013 | Fuller et al. | |
| 2013/0215376 A1 | 8/2013 | Guo et al. | |
| 2013/0238015 A1 | 9/2013 | Berdahl et al. | |
| 2013/0274638 A1 | 10/2013 | Jennings et al. | |
| 2014/0275935 A1 | 9/2014 | Walsh et al. | |
| 2015/0313761 A1 | 11/2015 | Berdahl et al. | |
| 2017/0049620 A1 | 2/2017 | Berdahl et al. | |

FOREIGN PATENT DOCUMENTS

| | | |
|---|---|---|
| WO | WO-2007136993 A1 | 11/2007 |
| WO | WO-2007139927 A1 | 12/2007 |
| WO | WO-2010006180 A1 | 1/2010 |
| WO | WO-2017035406 A2 | 3/2017 |
| WO | WO-2017035406 A3 | 3/2017 |

OTHER PUBLICATIONS

"U.S. Appl. No. 13/790,048, Non Final Office Action dated Jun. 24, 2014", 9 pgs.

"U.S. Appl. No. 13/790,048, Notice of Allowance dated May 4, 2015", 12 pgs.

"U.S. Appl. No. 13/790,048, Response filed Apr. 2, 2015 to Final Office Action dated Feb. 5, 2015", 11 pgs.

"U.S. Appl. No. 13/790,048, Response filed Sep. 24, 2014 to Non Final Office Action dated Jun. 24, 2014", 16 pgs.

"U.S. Appl. No. 14/800,018, Examiner Interview Summary dated Mar. 2, 2016", 3 pgs.

"U.S. Appl. No. 14/800,018, Non Final Office Action dated Sep. 25, 2015", 15 pgs.

"U.S. Appl. No. 14/800,018, Notice of Allowance dated Jul. 20, 2016", 11 pgs.

"U.S. Appl. No. 14/800,018, Preliminary Amendment filed Jul. 28, 2015", 5 pgs.

"U.S. Appl. No. 15/345,053, Preliminary Amendment filed Nov. 16, 2016", 5 pgs.

"U.S. Appl. No. 15/345,053, Supplemental Preliminary Amendment filed Aug. 21, 2017", 7 pgs.

"U.S. Appl. No. 15/688,016, Preliminary Amendment filed Aug. 29, 2017", 7 pgs.

"U.S. Appl. No. 14/800,018 Response filed Jan. 15, 2016 to Non-Final Office Action dated Sep. 28, 2015", 20 pgs.

"Cataract Surgery to Lower Intraocular Pressure", Middle East African Journal of Ophthalmology, 16 (3), (Sep. 2009), 1-5.

"Cerebrospinal Fluid Pressure Is Decreased in Primary Open-angle Glaucoma", American Academy of Ophthalmology, Manuscript No. 2007-1002, (2008), 763-768.

"International Application Serial No. PCT/US2016/048784, International Search Report dated Mar. 21, 2017", 9 pgs.

"International Application Serial No. PCT/US2016/048784, Invitation to Pay Additional Fees and Partial Search Report dated Nov. 28, 2016", 7 pgs.

"International Application Serial No. PCT/US2016/048784, Written Opinion dated Mar. 21, 2017", 10 pgs.

Alexander, David J., et al., "Risk of Spaceflight-Induced Intracranial Hypertension and Vision Alterations", Evidence Report—Version 1.0, (Jul. 12, 2012), 1-106.

Allin, David, et al., "Laboratory Testing of the Pressio Intracranial Pressure Monitor", Neurosurgery, vol. 62, vol. 5, [Online]. Retrieved from the Internet: <URL: www.neurosurgery-online.com, (May 2008), 1158-1161.

Araci, Ismail E., "An implantable microfuidic device for self-monitoring of intraocular pressure", nature medicine, vol. 20, No. 9—Technical Reports, (Sep. 2014), 1074-1080.

Berdahl, John P., et al., "Body Mass Index Has a Linear Relationship with Cerebrospinal Fluid Pressure", IOVS, vol. 53, No. 3, (Mar. 2012), 1422-1427.

Berdahl, John, "Cerebrospinal Fluid Pressure and Glaucoma", Glaucoma Today, (Oct. 2009), 14-18.

Berdahl, John P., et al., "Intracranial pressure and glaucoma", Current Opinion in Ophthalmology 21-, (2010), 106-111.

Berdahl, John P., et al., "Intracranial Pressure in Primary Open Angle Glaucoma, Normal Tension Glaucoma, and Ocluar Hypertension: A Case-Control Study", IOVS, vol. 49, No. 12, (Dec. 2008), 5412-5418.

Berdahl, John P., "Recovery of Corneal Hysteresis after Reduction of Intraocular Pressure in Chronic Primary Angle-Closure Glaucoma", American Journal of Ophthalmology—Correspondence, (Oct. 2009), 623-624.

Berdahl, John P., "Systemic Parameters Associated With Cerebrospinal Fluid Pressure", J Glaucoma, vol. 22, No. 5, Suppl 1, [Online]. Retrieved from the Internet: <URL: www.glaucomajournal.com, (Jul. 2013), S17-S18.

Berdahl, John P., "The translaminar pressure gradient in sustained zero gravity, idiopathic inracranial hypertension and glaucoma", Medical Hypotheses 79, (2012), 719-724.

Fleischman, David, et al., "Cerebrospinal Fluid Pressure Decreases with Older Age", PLOS One, vol. 7, Issue 12, [Online]. Retrieved from the Internet: <URL: www.plosone.org, (Dec. 2012), 1-9.

Fleischman, David, et al., "Increasing intraocular pressure as treatment for papilledema", Experimental Eye Research 115, (2013), 278.

(56) References Cited

OTHER PUBLICATIONS

Goel, Manik, et al., "Aqueous Humor Dynamics: A Review", The Open Ophthalmology Journal, [Online]. Retrieved from the Internet: <URL: http://www.ncbi.nlm.nih.gov/pmc/articles/PMC3032230>, (2010), 52-59.

Hayreh, Sohan Singh, "Cerebrospinal fluid pressure and glaucomatous optic disc cupping (response to Berdahl and colleagues)", Graefes Arch Clin Exp Opthtalmol, 247, (2009), 1291-1294.

Hillen; Mark; "In Practice (VIIP: A Space Odyssey)", The Ophthalmologist, vol. 11, (Sep. 2014), 30-34.

Jonas, Jost R., et al., "Anatomic Relationship between Lamina Cribrosa,Intraocular Space, and Cerebrospinal Fluid Space", Investigative Ophthalmology & Visual Science, Dec. 2003, vol. 44, No. 12, Investigative Ophthalmology & Visual Science, vol. 44, No. 12, (Dec. 2003), 5189-5195.

Jung, Jong Jin, et al., "Analysis of the Causes of Optic-Disc Swelling", Korean J Ophthalmol, 25 (1), (2011), 33-36.

Kent, Christopher, "IOP: Managing the Fluctuation Factor", Review of OPhthalmology, [Online]. Retrieved from the Internet: <URL: http://www.reviewofophthalmology.com/content/i/1533/c/28662/dnnprintmode/true/?skinsrc=[l]skins/rp2010/pageprint&containersrc=[l]containers/rp2010/blank, (Jun. 13, 2011), 6 pgs.

Morgan, William H., et al., "Retinal venous pulsation: Expanding our understanding and use of this enigmatic phenomenon", Progress in Retinal and Eye Research xxx, (2016), 1-26.

Wostyn, Peter, et al., "Glaucoma and the Role of Cerebrospinal Fluid Dynamics", Investigative Ophthalmology & Visual Sciences, (2015), 6630.

Yeoh, Ronald, "Hydrorupture of the posterior capsule in femtosecond-laser cataract surgery", J Cataract Refract Surg, vol. 38, (Apr. 2012), 730-731.

Young, Joshua, "ASFH CSF Pressure and Glaucoma (Guest: John P. Berdahl, M.D.)", As Seen From Here: 198 (Podcast—iTunes) (Transcribed), (Jul. 8, 2008), Run time: 15:14 Minutes.

Zhang, Zheng, et al., "Glaucoma and the Role of Cerebrospinal Fluid Dynamics", Investigative Ophthalmology & Visual Sciences, (2015), 6632.

"U.S. Appl. No. 15/688,016, Final Office Action dated May 15, 2018", 11 pgs.

"U.S. Appl. No. 15/688,016, Response filed Jun. 12, 2018 to Final Office Action dated May 15, 2018", 10 pgs.

"U.S. Appl. No. 15/754,723, Preliminary Amendment filed Feb. 23, 2018", 8 pgs.

"U.S. Appl. No. 15/912,872, Non Final Office Action dated Jun. 8, 2018", 13 pgs.

"International Application Serial No. PCI7US2016/048784, International Preliminary Report on Patentability dated Mar. 8, 2018", 12 pgs.

"U.S. Appl. No. 15/688,016, Non Final Office Action dated Oct. 20, 2017", 16 pgs.

"U.S. Appl. No. 15/688,016, Response filed Jan. 16, 2018 to Non Final Office Action dated Oct. 20, 2017", 9 pgs.

"Australian Application Serial No. 2016311449, First Examination Report dated Jul. 27, 2018", 4 pgs.

"U.S. Appl. No. 15/688,016, Advisory Action dated Jul. 25, 2018",4 pgs.

"U.S. Appl. No. 15/688,016, Response filed Aug. 15, 2018 to Advisory Action dated Jul. 25, 2018", 9 pgs.

U.S. Appl. No. 15/912,872, filed Mar. 6, 2018, Intraocular Pressure Modification for Treating Glaucoma.

* cited by examiner

US 10,154,926 B1

METHODS OF USING EYE MONITORING AND PRESSURIZATION SYSTEMS

CLAIM OF PRIORITY

The present application is a Continuation Application of U.S. patent application Ser. No. 15/345,053 filed Nov. 7, 2016, which is a continuation of U.S. patent application Ser. No. 14/800,018 filed Jul. 15, 2015, which is a continuation of U.S. patent application Ser. No. 13/790,048 filed Mar. 8, 2013, which claims the benefit of priority under 35 U.S.C. § 119(e) to U.S. Provisional Patent Application Ser. No. 61/609,078, filed on Mar. 9, 2012, and which all are titled "INTRAOCULAR PRESSURE MODIFICATION," and which are hereby both incorporated by reference in their entirety.

TECHNICAL FIELD

This patent document pertains generally to ocular treatments. More particularly, but not by way of limitation, this patent document pertains to modifying an intraocular pressure of a patient's one or both eyes.

BACKGROUND

Glaucoma is a common chronic condition predominantly affecting members of the elderly population. Glaucoma is a top cause of blindness worldwide and it is the leading cause of irreversible blindness worldwide. While glaucoma is not reversible, its progression can be stopped or slowed with treatment.

Most existing glaucoma treatments fall into one of two categories: eye drop medications or invasive surgeries.

Eye drop medication (e.g., prostaglandins, beta blockers, carbonic anhydrate inhibitors, or alpha agonists) is typically the first treatment option since it can be effective for many patients and have relatively low complication rates. Still, a significant number of patients (e.g., about 20% of patients) exist for whom eye drop medication is ineffective. There is also a significant problem with patient compliance in taking eye drop medication on a regular basis. Since glaucoma is a chronic condition and is not currently curable, glaucoma patients need to take their eye drop medication for the rest of their lives. It has been estimated that up to 50% of glaucoma patients prescribed with an eye drop medication fail to successfully administer their drops on a regular basis. This failure can be due to forgetting, difficulty getting the drops in one's eyes, reluctance to take long-term medications, or unhappiness with certain side effects (e.g., redness of the eyes, eyelash growth, inflammation, orbital fat atrophy, discoloration of the iris or surrounding periorbital tissues, exacerbation of COPD or asthma, inhibition of corneal endothelial pump function, exacerbation of corneal edema, or stinging upon instillation).

Various surgical options (e.g., laser trabeculoplasty, trabecular meshwork stents, suprachoroidal stents, subconjunctival stents or trabeculectomy or glaucoma tube shunts) are typically the second treatment option for glaucoma patients. Surgical options are more invasive and have can higher complication and morbidity rates as compared to eye drop medication treatments.

OVERVIEW

While glaucoma is not reversible, its progression can be stopped or slowed with treatment directed to reducing intraocular pressure ("IOP"). The present inventors have recognized, among other things, that there is a need for a new non-invasive method of controlling IOP that does not rely on eye drop medication. This need is due to issues associated with eye drop medication compliance, the significant number of patients for whom eye drop medication is ineffective, and complication and morbidity rates of surgery. The present invention provides assemblies and methods for modifying IOP in a patient's one or both eyes without the need for invasive therapies or use of medications.

The assemblies and methods include variations of a goggle or goggles configured to fit over one or both of a patient's eyes and means to alter a pressure inside one or more cavities of the goggle or goggles. An outer surface of the goggle or goggles can seal against a patient's skin around a perimeter of his/her eye sockets. Subsequently, when the means to alter pressure is actuated, a pressure differential from atmospheric pressure can be created and maintained inside the one or more goggle cavities and over one or both of the eyes. The cavity pressure can be either increased or decreased relative to atmospheric pressure, depending on a condition being treated (e.g., whether glaucoma is being treated or whether papilledema is being treated). The change in pressure outside of the eye(s) can act to alter a pressure inside the eye(s) (e.g., IOP) through a resulting deflection of the shape of the eye(s), by driving a change in a rate of drainage of eye fluids through a trabecular meshwork, and/or from the pressure difference being directly translated into the eye(s). The pressure can be altered by use of a small compressor or vacuum device (collectively a "pump") in fluid communication with the one or more cavities of the goggle or goggles.

According to a first embodiment of an assembly, a goggle or goggles can be configured to fit over one or both eyes of a patient and seal against the skin, around the eye sockets. The goggle or goggles can be sufficiently air tight to allow a desired air pressure to be maintained in one or more cavities inside the goggle or goggles and over the eye(s). The mechanism to alter the pressure inside the goggle cavities can be a portable reversible pump mounted to the goggle or goggles and in fluid communication with one or both sides of the goggle or goggles. The power supply for the pump can be a rechargeable or other battery integral to the goggle or goggles. The pump element can be actuated, manually or through programming, by the patient or a caregiver physician to obtain a desired cavity pressure. To facilitate creation of the desired cavity pressure, the pump can include a variable setting and/or the assembly can include one or more vents.

According to a second embodiment of an assembly, a goggle or goggles can be configured to fit over one or both eyes and seal against the skin around the eye sockets. A small reversible pump having vacuum and pressure pump capabilities can be mounted remote to the goggle or goggles and connected to one or more cavities inside the goggle or goggles with one or more elongate tubes. The power supply for the pump system can be a wall plug or a battery pack. The remote vacuum and/or pressure pump can be set by the patient or the caregiver physician for a desired pressure level, and can include a pressure measuring component to allow automatic closed loop control of the pressure level.

According to a third embodiment of an assembly, a goggle or goggles can be configured similar to the second embodiment, but further include a pressure control mechanism in electronic communication with one or more biosensors. The biosensors can be configured to monitor the IOP and/or the cerebrospinal fluid ("CSF") pressure (or surrogates for these anatomic pressures). The biosensor monitoring can allow the goggle cavity pressure to be controlled to a target level determined by the real time measured values for IOP and/or CSF pressure.

According to yet another embodiment of an assembly, the target pressure inside one or more cavities of a goggle or goggles can be altered in a desired sequence to optimize a desired change in the IOP. For example, it may be beneficial to cycle the pressure inside the goggle cavities to increase the "pumping" action being driven through the trabecular meshwork and into the anterior ciliary veins. By increasing the "pumping" action, a greater decrease in the IOP can be achieved in a shorter amount of time. Some users may find it desirable to minimize the time that the goggle or goggles need to be worn. Optionally, the assembly, and specifically one or more cavities of the goggle or goggles, can be configured to isolate the pressure effect over the trabecular meshwork or the anterior ciliary veins of an eye to isolate the pressure effects. A cavity of the goggle or goggles can, for example, be segregated into distinct subcategories providing pressure effects to certain portions of an eye (e.g., front portions of the eye) and not result in broader eye remodeling.

It is believed that the assemblies can be worn during the day, during the night, or for short durations throughout the day or night. The appropriate duration and frequency of pressure modulation can vary depending on the condition being treated. By lowering IOP and equalizing a translaminar pressure gradient (e.g., if CSF pressure is low), axonal transport can resume to meet metabolic needs of an optic nerve. Alternatively, raising IOP can equalize the translaminar pressure gradient (e.g., if the CSF pressure is high) and can allow axonal transport to resume. This physiological improvement of axonal transport resumption can have lasting benefit for the optic nerve by allowing the temporary resumption of normal metabolic functions, even if the IOP reverts to the atmospheric pressure after the goggle or goggles are removed.

Normal IOP is in the range of 10-21 mmHG, while normal CSF pressure is in the range of 8-20 mmHG. The goggle or goggles can, in some examples, induce vacuum IOP up to 50 mmHG and can increase CSF pressure up to 50 mmHG.

These and other examples and features of the present assemblies and methods related to the assemblies will be set forth in part in following Detailed Description. This Overview is intended to provide non-limiting examples of the present subject matter—it is not intended to provide an exclusive or exhaustive explanation. The Detailed Description below is included to provide further information about the present assemblies and methods.

BRIEF DESCRIPTION OF THE DRAWINGS

In the drawings, like numerals can be used to describe similar elements throughout the several views. Like numerals having different letter suffixes can be used to represent different views of similar elements. The drawings illustrate generally, by way of example, but not by way of limitation, various embodiments discussed in the present document.

DETAILED DESCRIPTION

Figure 1:
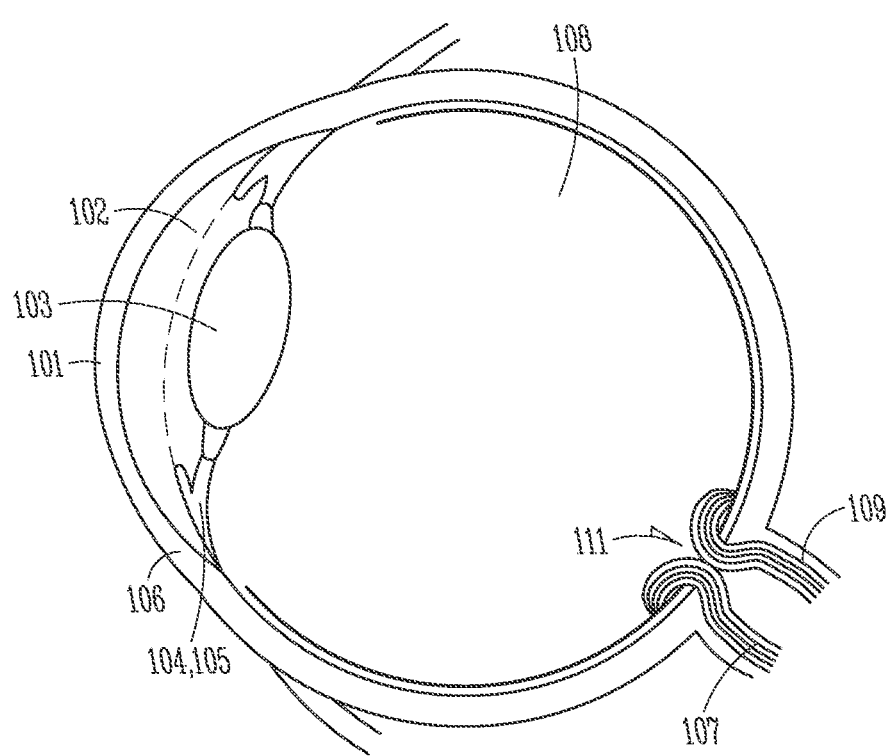
FIG. 1 illustrates a side cross-sectional view of an eye.

FIG. 1 illustrates ocular structures in cross-section, which provide a suitable environment for using the present assemblies and methods. A front surface of an eye is a cornea 101. Located behind the cornea 101 is an anterior chamber or aqueous chamber 102. This is the primary reservoir of aqueous humor inside the eye. Located behind the anterior chamber 102 is a lens 103, and behind and around the lens 103 are ciliary processes 105. The ciliary processes 105 are areas of the eye where aqueous humor is produced. The ciliary muscle 104 is roughly in the same plane as the lens 103 and is positioned around the perimeter of the lens 103. A trabecular meshwork 106, Schlemm's canal, and anterior ciliary veins are all located below the anterior chamber 102 at the bottom of the cornea 101. This is the primary pathway for aqueous humor to exit the eye.

Behind the lens 103 and the ciliary processes 105 is the posterior chamber of the eye filled with viscous humor 108. The viscous humor 108 is distinct from the aqueous humor, but the separation between the chambers holding such fluids is elastic and, as such, the pressures of the two different humor fluids are equal or approximately equal. An optic nerve 107 connects to the back of the eye. A lamina cribrosa 111 is the membrane over the junction of the optic nerve 107 and the eye. Cerebrospinal fluid 109 baths the optic nerve 107 behind the lamina cribrosa 111 so that the lamina cribrosa is impacted on one side by the cerebrospinal fluid 109 pressure and on the other by the IOP.

During normal function of an eye, aqueous humor is produced inside the eye by the ciliary processes 105 in an anterior segment of the eye. As aqueous humor is steadily produced, a like amount of fluid must exit from the anterior chamber 102 of the eye to maintain a balanced eye pressure. The aqueous humor can exit the anterior chamber 102 by one or both of two main pathways. Some is reabsorbed by the uveoscleral outflow tract around the ciliary muscles 104. Some exits the eye though the trabecular meshwork 106, a porous region in the front of the eye located between the cornea 101 and iris insertion. The aqueous fluid that exits via the trabecular meshwork flows through Schlemm's canal into the anterior ciliary veins. The present assemblies and methods can modify the IOP in a patient's one or both eyes by altering the flow rate of aqueous humor across the trabecular meshwork 106, Schlemm's canal, and the anterior ciliary vein pathway.

Figure 2:
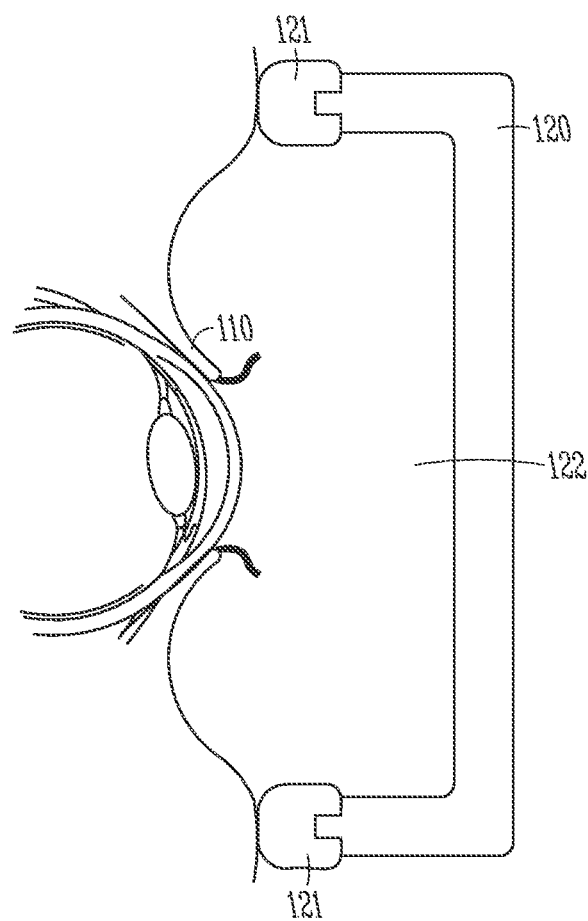
FIG. 2 illustrates a side schematic view of an assembly, as constructed in accordance with at least one embodiment, positioned in front of an eye.

FIG. 2 illustrates a side schematic view of an assembly, as constructed in accordance with at least one embodiment, positioned in front of an eye. The assembly can include a goggle or goggles 120, shown in cross-section, including one or more cavities 122. The body of the goggle or goggles 120 can be relatively rigid and made of an impermeable clear plastic so that it can maintain the differential pressure inside the goggle or goggles, while allowing a patient wearing the goggle or goggles to see outward. There can be a seal material 121 positioned around a perimeter of the goggle body, which can create a seal between edges of the goggle or goggles and the patient's skin around the eyes. The seal material can be a softer rubber or plastic wiper held in close contact with the skin by a strap around the head (not shown). The seal material can alternatively be made of a compressible foam material, for example.

The cavity area 122 inside the goggle or goggles 120 can have its air pressure altered by components of the assembly. The eye lid 110 is shown over the front of the eye. It can be seen in the schematic illustration of FIG. 2 that the altered air pressure in the cavity area 122 can act on the entire area in front of the eye. This altered pressure can be a reduced air pressure for patients with glaucoma or high IOP so that it acts to decrease the IOP. The altered pressure can be an increased air pressure for patients with optic disk edema (swelling of the lamina cribrosa—see closing notes, below). The assembly can also be configured to allow the altered pressure to be varied over time to different target levels if such configuration is found to be clinically desirable.

Bench testing utilizing the aforementioned techniques was conducted to investigate an effect on IOP of a vacuum applied to a convex surface of a human cadaver eye. The experimental model involved mounting a front half of an incised eye to an inside surface of a pressure vessel. A seal was created between a perimeter of the incision and a surface of the pressure vessel so that the inside of the incised eye could be pressurized to a specified pressure or flow rate to simulate IOP. The pressure vessel was then sealed, the initial IOP recorded, and vacuum steps of 10 and 20 mmHg applied to the control volume above the convex surface of the incised eye. The final IOP resulting from each vacuum step was then recorded. Note that the lens of the incised eye had been removed and, while the trabecular meshwork was intact and functional, the urio scleral pathway and scleral muscles were not functional.

Figure 3:
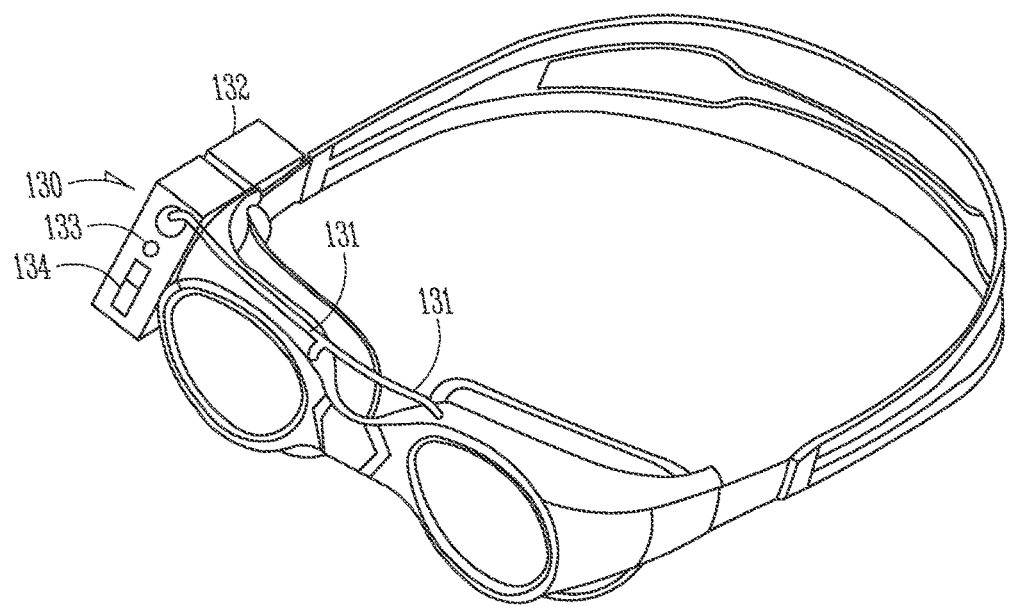
FIG. 3 illustrates an isometric view of an assembly, as constructed in accordance with at least one embodiment.

Two bench tests using this experimental model were conducted. In a first test, an initial IOP of 24.3 mmHg was reduced to 19.3 mmHg and 9.1 mmHg for applied vacuums of 10 mmHg and 20 mmHg, respectively, returning to 28.3 mmHg upon release of the vacuum. In a second test, an initial IOP of 28.3 mmHg was reduced to 19.4 mmHg and 10.4 mmHg for applied vacuums of 10 mmHg and 20 mmHg, respectively, returning to 28.9 mmHg upon release of the vacuum. FIG. 3 illustrates an isometric view of an assembly in which a pressure control mechanism is mounted to a pair of goggles. The pressure control mechanism can include a pressure/vacuum pump 130. This pump 130 can be a compressor, a vacuum pump, or configured to be reversible so that the same goggles can be used for either raising or lowering the pressure inside goggle cavities. The pressure/vacuum pump 130 can be in fluid communication with the inside of the goggles through one or more pressure tubes 131. Power for the pressure/vacuum pump 130 can be supplied by a battery pack 132. The pressure/vacuum pump can be actuated by means of an on/off switch 134. A set point or rage for the target pressure can be set by means of an adjustable dial 133. The adjustable pressure set point or range can control the pressure in a closed loop manner when a pressure sensor monitoring the pressure in the goggle cavities is used. Other means in which the adjustable pressure set point or range can be maintained include controlling a speed of the pump 130 or controlling a vent in the assembly so that only a portion of the fixed speed pump is acting on the area inside the goggle cavities.

Figure 4:
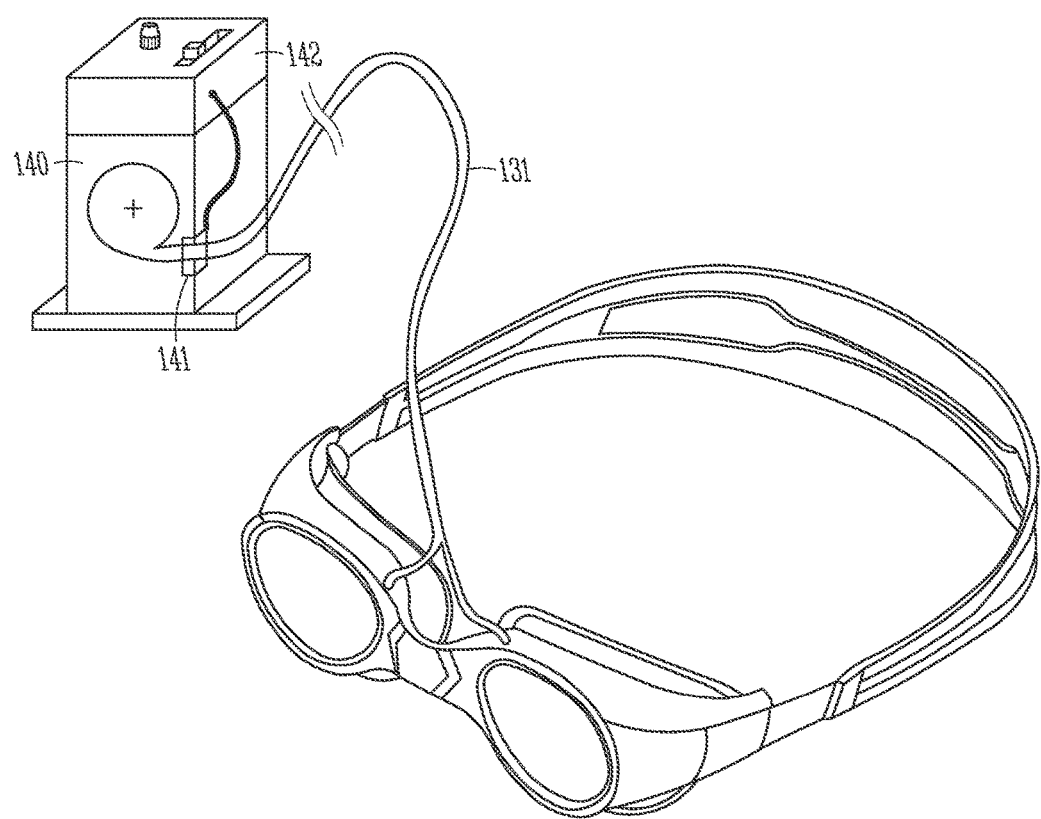
FIG. 4 illustrates an isometric view of an assembly, as constructed in accordance with at least one other embodiment.

FIG. 4 illustrates an isometric view of an assembly in which a pressure control mechanism is mounted remote to the goggles. A pressure/vacuum pump 140 can be set on a side table and plugged into a wall socket for power while the patient is sleeping or otherwise sedentary. The pressure/vacuum pump 140 can also be clipped to a belt and powered with a battery pack if the patient desires to be mobile. In the illustrated example, a pressure sensor 141 and a pressure control box 142 are shown. The pressure control box 142 can include the same or similar options of control as described in association with FIG. 3. The pressure sensor 141 can be used if the control method used is closed loop based on a monitored pressure.

Optionally, the pressure control target set point or range can be varied by the pressure control box 142 in response to a signal sent from another sensor monitoring the patient's IOP and/or CSF pressure or surrogates for one or both pressures. In this way, the pressure inside the goggle cavities can be controlled to yield a targeted IOP based on real time measurement of the IOP or CSF pressure.

To further describe the present assemblies and methods, a non-limiting list of examples is provided here:

In Example 1, an assembly can comprise a goggle, a pump, and a control mechanism. The goggle can include at least one cavity and can be configured to surround and be spaced from an eye. The pump can be in fluid communication with the at least one cavity. The control mechanism can be operatively coupled to the pump, and can be configured to receive a target pressure setting and maintain the target pressure in the at least one cavity through activation or deactivation of the pump.

In Example 2, the assembly of Example 1 can optionally be configured such that the goggle can include a set of goggles including a first cavity and a second cavity, the second cavity being spaced from the first cavity.

In Example 3, the assembly of Example 2 can optionally be configured such that the pump is in fluid communication with the first cavity and the second cavity.

In Example 4, the assembly of any one or any combination of Examples 1-3 can optionally be configured such that the pump includes one or both of a compressor device or a vacuum device.

In Example 5, the assembly of any one or any combination of Examples 1-4 can optionally further comprise at least one transducer configured to measure a pressure in the at least one cavity and electronically communicate the pressure to the control mechanism.

In Example 6, the assembly of Example 5 can optionally be configured such that the at least one transducer is a pressure sensor configured to monitor an intraocular pressure or a cerebrospinal fluid pressure.

In Example 7, the assembly of any one or any combination of Examples 1-6 can optionally be configured such that the control mechanism comprises a control circuit configured to initiate a therapy cycle to the at least one cavity based, in part, on the target pressure setting.

In Example 8, the assembly of any one or any combination of Examples 1-7 can optionally further comprise a battery configured to provide power to operate the pump and the control mechanism.

In Example 9, the assembly of any one or any combination of Examples 1-8 can optionally be configured such that the goggle includes one or more vents fluidly coupling the at least one cavity and a surrounding environment.

In Example 10, the assembly of any one or any combination of Examples 1-9 can optionally further comprise a seal member coupled to a perimeter of the goggle.

In Example 11, a method can comprise placing an assembly, including a goggle having at least one cavity, a pump in fluid communication with the at least one cavity, and a control mechanism, over and around an eye, including spacing the goggle from a surface of the eye; setting a target pressure within the at least one cavity using the control mechanism; establishing the target pressure within the at least one cavity; and maintaining the target pressure within the at least one cavity for a period of time.

In Example 12, the method of Example 11 can optionally further comprise adjusting the target pressure.

In Example 13, the method of any one or any combination of Examples 11 or 12 can optionally further comprise adjusting the target pressure based, at least in part, upon measurement of at least one physiological parameter.

In Example 14, the method of any one or any combination of Examples 11-13 can optionally be configured such that establishing the target pressure includes creating a pressure differential from atmospheric pressure in the at least one cavity.

In Example 15, the method of Example 14 can optionally be configured such that creating the pressure differential from atmospheric pressure in the at least one cavity includes changing a shape of the eye or changing a rate of drainage of an eye fluid through a trabecular meshwork associated with the eye.

In Example 16, the method of any one or any combination of Examples 11-15 can optionally be configured such that maintaining the target pressure includes delivering a predetermined therapeutic pressure cycle to the eye.

In Example 17, the method of any one or any combination of Examples 11-16 can optionally be configured such that maintaining the target pressure includes maintaining a pressure in an operating range from −40 mmHg to 40 mmHg (gage).

In Example 18, the method of Example 17 can optionally be configured such that maintaining the pressure in the operating range includes maintaining the pressure in an operating range from 5 mmHg to 20 mmHg (gage).

In Example 19, the method of any one or any combination of Examples 11-18 can optionally be configured such that maintaining the target pressure includes reducing an intraocular pressure of the eye.

In Example 20, the method of any one or any combination of Examples 11-19 can optionally be configured such that maintaining the target pressure includes inhibiting a progression of glaucoma associated with the eye.

ELEMENT NUMERAL LIST

- 101—Cornea
- 102—Anterior chamber (aqueous chamber)
- 103—Lens
- 104—Ciliary muscle
- 105—Ciliary processes
- 106—Trabecular meshwork, Schlemm's canal, anterior ciliary veins (all in close proximity)
- 107—Optic nerve
- 108—Viscous humors
- 109—Cerebrospinal fluid around optic nerve
- 110—Eye lid
- 111—Lamina cribrosa
- 120—Goggle body
- 121—Seal material around goggle perimeter
- 122—Cavity area inside goggle having an altered pressure
- 130—Pressure and/or vacuum pump (collectively referred to as a "pump")
- 131—One or more fluid lines connecting a pump to a goggle cavity area
- 132—Rechargeable battery pack
- 133—Pressure adjusting control dial including a control circuit (embodiment of "control mechanism")
- 134—On/Off switch
- 140—Remote mounted pressure and/or vacuum pump
- 141—Pressure sensor
- 142—Pressure control box including a control circuit (embodiment of "control mechanism")

CLOSING NOTES

High IOP is a cause of glaucoma. Recent studies are showing that there may be other causes of glaucoma in addition to IOP. IOP and other causes of glaucoma, including CSF pressure and optic disc edema, are believed to be treatable using the present assemblies and methods.

Cerebrospinal fluid bathes the spinal cord, brain, and optic nerve. The optic nerve is surrounded by CSF as it exits the intracranial vault and passes through the orbit and is present all the way up to the termination of the optic nerve as it enters the lamina cribrosa posterior in the eye. Glaucoma occurs at the optic nerve in the lamina cribrosa. Since CSF bathes the optic nerve all the way to its entry in the eye, it is reasonable to conclude that both pressurized fluids, IOP and CSF, exposed to the optic nerve can contribute to glaucoma and can be treated using the present assemblies and methods.

Studies have shown that CSF pressure is low in patients with glaucoma. The CSF pressure is even lower in patients that have normal-tension glaucoma and is higher and potentially protective in people that have ocular hypertension. These findings are consistent with the findings seen in glaucomatous optic nerves where the optic nerve is bowed and the lamina cribrosa are bowed posterior. This is possibly caused by an IOP that is higher than a CSF pressure creating a net force on the lamina cribrosa that slowly remodels with time. It is also the opposite of what is seen in idiopathic intracranial hypertension where elevated CSF pressure causes swelling and anterior bulging of the optic nerve.

If further testing shows that CSF is in fact a significant risk factor for glaucoma in concert with IOP, then there can be a need for a glaucoma treatment similar to the present assemblies and methods that can be titrated to an appropriate level based on these two anatomic pressures for a patient.

Another condition effecting vision and related to these same anatomic pressures is optic disk edema or swelling. It is to be expected that the CSF pressure at the level of the eye can increase in a zero gravity environment as the eye is relatively high in the CSF cavity (spinal cord, brain, optic nerve). In a gravity environment, the CSF pressure is higher in the caudal portion of the spinal cord due to gravity (analogous to pressure increasing as you go deeper under water). In zero gravity, this effect is not present, resulting in a relatively higher CSF pressure at the height of the optic nerve.

Optic disk edema also is seen in other patients possibly due to high CSF pressure relative to IOP. For these patients, there can be a need for a treatment such as the present assemblies and methods that enable increasing the IOP to a targeted pressure relative to the CSF pressure to return the patients to a normal differential pressure across the lamina cribrosa.

The above Detailed Description includes references to the accompanying drawings, which form a part of the Detailed Description. The drawings show, by way of illustration, specific embodiments in which the present assemblies and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description (e.g., a goggle or goggles including a single cavity or goggles having distinct cavities for each eye). Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method to treat, inhibit, or prevent an eye condition in a patient experiencing a symptom of glaucoma, comprising:
   providing a system, the system including a goggle defining a cavity, the goggle sized and shaped to fit over an eye of a patient, a biosensor configured to monitor an indication of a physiological parameter associated with the eye of the patient, and a pressure source, in fluidic communication with the cavity, configured to pressurize the cavity;
   monitoring the physiological parameter associated with the eye of the patient with the biosensor, the monitored physiological parameter including at least one of an indication of IOP or CSF pressure; and
   pressurizing the cavity to a non-ambient pressure less than ambient pressure including controlling the pressure source to generate in the cavity a non-ambient pressure that is less than an ambient pressure outside the cavity based on at least one of an indication of IOP or CSF pressure monitored with the biosensor.

2. The method of claim 1, wherein controlling the pressure source to generate the non-ambient pressure includes controlling the pressure source to generate the non-ambient pressure based on the indication of IOP monitored with the biosensor.

3. The method of claim 2, wherein controlling the pressure source to generate the non-ambient pressure includes controlling the pressure source to generate the non-ambient pressure to achieve an indication of a target IOP level in the eye of the patient monitored with the biosensor.

4. The method of claim 3, wherein controlling the pressure source to achieve an indication of a target IOP level in the eye with the biosensor includes controlling the pressure source to adjust the target IOP level in the eye monitored with the biosensor.

5. The method of claim 4, wherein controlling the pressure source to adjust the target IOP level in the eye includes controlling the pressure source to adjust the target IOP level in the eye in a desired sequence.

6. The method of claim 5, wherein controlling the pressure source to adjust the target IOP level in the eye in a desired sequence includes controlling the pressure source to deliver a predetermined pressure cycle to the eye.

7. The method of claim 1, wherein controlling the pressure source to generate the non-ambient pressure includes controlling the pressure source to generate the non-ambient pressure based on the indication of CSF pressure monitored with the biosensor.

8. The method of claim 1, wherein pressurizing the cavity to the non-ambient pressure includes controlling the pressure source to equalize translaminar pressure in the eye of the patient based on at least one of the indication of IOP or the indication of CSF pressure monitored with the biosensor.

9. The method of claim 8, wherein controlling the pressure source to equalize translaminar pressure in the eye based on at least one of the indication of IOP or CSF pressure monitored with the biosensor includes controlling the pressure source to equalize translaminar pressure in the eye based on the indication of IOP.

10. The method of claim 1, comprising maintaining the non-ambient pressure in the cavity to be less than ambient pressure outside the cavity for a period of time to treat glaucoma in the eye of the patient.

11. A method to treat, inhibit, or prevent an eye condition in a patient experiencing a symptom of optic disc edema, comprising:
    providing a system, the system including a goggle defining a cavity, the goggle sized and shaped to fit over an eye of a patient, a biosensor configured to monitor an indication of a physiological parameter associated with the eye of the patient, and a pressure source, in fluidic communication with the cavity, configured to pressurize the cavity;
    monitoring the physiological parameter associated with the eye of the patient with the biosensor, the monitored physiological parameter including at least one of an indication of IOP or CSF pressure; and
    pressurizing the cavity to a non-ambient pressure greater than ambient pressure outside the cavity, the pressurizing including controlling the pressure source to generate the non-ambient pressure based on at least one of an indication of IOP or CSF pressure monitored with the biosensor.

12. The method of claim 11, wherein controlling the pressure source to generate the non-ambient pressure includes controlling the pressure source to generate the non-ambient pressure based on the indication of IOP monitored with the biosensor.

13. The method of claim 12, wherein controlling the pressure source to generate the non-ambient pressure includes controlling the pressure source to generate the non-ambient pressure to achieve an indication of a target IOP level in the eye of the patient monitored with the biosensor.

14. The method of claim 13, wherein controlling the pressure source to achieve an indication of a target IOP level in the eye with the biosensor includes controlling the pressure source to adjust the target IOP level in the eye monitored with the biosensor.

15. The method of claim 14, wherein controlling the pressure source to adjust the target IOP level in the eye includes controlling the pressure source to adjust the target IOP level in the eye in a desired sequence.

16. The method of claim 15, wherein controlling the pressure source to adjust the target IOP level in the eye in a desired sequence includes controlling the pressure source to deliver a predetermined pressure cycle to the eye.

17. The method of claim 11, wherein controlling the pressure source to generate the non-ambient pressure includes controlling the pressure source to generate the non-ambient pressure based on the indication of CSF pressure monitored with the biosensor.

18. The method of claim 11, wherein pressurizing the cavity to the non-ambient pressure includes controlling the pressure source to equalize translaminar pressure in the eye of the patient based on at least one of the indication of IOP or the indication of CSF pressure monitored with the biosensor.

19. The method of claim 18, wherein controlling the pressure source to equalize translaminar pressure in the eye based on at least one of the indication of IOP or CSF pressure monitored with the biosensor includes controlling the pressure source to equalize translaminar pressure in the eye based on the indication of IOP.

20. The method of claim 11, comprising maintaining the non-ambient pressure in the cavity to be greater than ambient pressure outside the cavity for a period of time to treat optic disk edema in the eye of the patient.

* * * * *